(12) United States Patent
Xia et al.

(10) Patent No.: US 8,376,937 B2
(45) Date of Patent: Feb. 19, 2013

(54) TISSUE MONITORING SURGICAL RETRACTOR SYSTEM

(75) Inventors: Jusong Xia, Collierville, TN (US); Joseph Jude Saladino, Memphis, TN (US); Jeff R. Justis, Germantown, TN (US); Newton H. Metcalf, Jr., Memphis, TN (US); Greg C. Marik, Collierville, TN (US); Nikolas F. Kerr, Germantown, TN (US); Hai H. Trieu, Cordova, TN (US)

(73) Assignee: Warsaw Orhtopedic, Inc., Warsaw, IN (US)

( * ) Notice: Subject to any disclaimer, the term of this patent is extended or adjusted under 35 U.S.C. 154(b) by 191 days.

(21) Appl. No.: 12/695,211

(22) Filed: Jan. 28, 2010

(65) Prior Publication Data
US 2011/0184245 A1     Jul. 28, 2011

(51) Int. Cl.
*A61B 1/32* (2006.01)
(52) U.S. Cl. ........................................... 600/202
(58) Field of Classification Search ........... 600/184–246
See application file for complete search history.

(56) References Cited

U.S. PATENT DOCUMENTS

| | | | |
|---|---|---|---|
| 2,456,806 A * | 12/1948 | Wolffe | 33/512 |
| 4,813,435 A | 3/1989 | Arms | |
| 4,993,428 A | 2/1991 | Arms | |
| 5,016,631 A | 5/1991 | Hogrefe | |
| 5,083,573 A | 1/1992 | Arms | |
| 5,125,408 A | 6/1992 | Basser | |
| 5,197,488 A | 3/1993 | Kovacevic | |
| 5,289,826 A | 3/1994 | Kovacevic | |
| 5,360,016 A | 11/1994 | Kovacevic | |
| 5,425,775 A | 6/1995 | Kovacevic | |
| 5,456,724 A | 10/1995 | Yen et al. | |
| 5,470,354 A | 11/1995 | Hershberger et al. | |
| 5,694,946 A | 12/1997 | Tenerz et al. | |
| 5,695,496 A | 12/1997 | Orsak et al. | |
| 5,769,781 A * | 6/1998 | Chappuis | 600/202 |
| 5,777,467 A | 7/1998 | Arms et al. | |
| 5,810,735 A | 9/1998 | Halperin et al. | |
| 5,833,603 A | 11/1998 | Kovacs et al. | |
| 6,034,296 A | 3/2000 | Elvin et al. | |
| 6,059,784 A | 5/2000 | Perusek | |
| 6,292,680 B1 | 9/2001 | Somogyi et al. | |
| 6,416,474 B1 | 7/2002 | Penner et al. | |
| 6,432,050 B1 | 8/2002 | Porat et al. | |
| 6,447,448 B1 | 9/2002 | Ishikawa et al. | |
| 6,475,170 B1 | 11/2002 | Doron et al. | |
| 6,486,588 B2 | 11/2002 | Doron et al. | |
| 6,529,127 B2 | 3/2003 | Townsend et al. | |
| 6,533,733 B1 | 3/2003 | Ericson et al. | |

(Continued)

FOREIGN PATENT DOCUMENTS

EP          1442715 A2      8/2004

*Primary Examiner* — Eduardo C Robert
*Assistant Examiner* — Mary Hoffman

(57) ABSTRACT

An apparatus for monitoring the characteristics of tissue adjacent a surgical site and communicating that information to a health care provider includes a retractor, a sensor, and a processing system. The sensor is disposed on the retractor and is configured to measure a parameter indicative of at least one characteristic of the tissue adjacent the first or the second blade. The processing system is in communication with the sensor and configured and arranged to receive information from the sensor indicative of the measured parameter. It includes a threshold stored therein indicative of excessive trauma to the tissue and it is configured in a manner such that it compares the received information to the stored threshold and communicates information to the health care provider regarding the comparison.

16 Claims, 8 Drawing Sheets

U.S. PATENT DOCUMENTS

| | | |
|---|---|---|
| 6,610,096 B2 | 8/2003 | MacDonald |
| 6,628,989 B1 | 9/2003 | Penner et al. |
| 6,706,005 B2 | 3/2004 | Roy et al. |
| 6,706,071 B1 | 3/2004 | Wolter |
| 6,761,741 B2 | 7/2004 | Iesaka |
| 6,764,446 B2 | 7/2004 | Wolinsky et al. |
| 6,802,811 B1 | 10/2004 | Slepian |
| 6,810,753 B2 | 11/2004 | Valdevit et al. |
| 6,821,299 B2 | 11/2004 | Kirking et al. |
| 6,889,165 B2 | 5/2005 | Lind et al. |
| 7,001,393 B2 | 2/2006 | Schwenke et al. |
| 7,097,662 B2 | 8/2006 | Evans, III et al. |
| 7,582,058 B1 * | 9/2009 | Miles et al. .................. 600/202 |
| 7,632,283 B2 | 12/2009 | Heldreth |
| 2002/0024450 A1 | 2/2002 | Townsend et al. |
| 2002/0045921 A1 | 4/2002 | Wolinsky et al. |
| 2003/0040806 A1 | 2/2003 | MacDonald |
| 2003/0069644 A1 | 4/2003 | Kovacevic et al. |
| 2003/0088157 A1 * | 5/2003 | Vassiliades et al. ......... 600/202 |
| 2003/0139690 A1 | 7/2003 | Aebli et al. |
| 2004/0011137 A1 | 1/2004 | Hnat et al. |
| 2004/0019382 A1 | 1/2004 | Amirouche et al. |
| 2004/0129095 A1 | 7/2004 | Churchill et al. |
| 2004/0152972 A1 | 8/2004 | Hunter |
| 2004/0186396 A1 | 9/2004 | Roy et al. |
| 2004/0204647 A1 | 10/2004 | Grupp et al. |
| 2004/0204744 A1 | 10/2004 | Penner et al. |
| 2005/0010302 A1 | 1/2005 | Dietz et al. |
| 2005/0027192 A1 | 2/2005 | Govari et al. |
| 2005/0165317 A1 | 7/2005 | Turner et al. |
| 2005/0234555 A1 | 10/2005 | Sutton et al. |
| 2006/0032314 A1 | 2/2006 | Hnat et al. |
| 2006/0036246 A1 | 2/2006 | Carl et al. |
| 2006/0036256 A1 | 2/2006 | Carl et al. |
| 2006/0036259 A1 | 2/2006 | Carl et al. |
| 2006/0036323 A1 | 2/2006 | Carl et al. |
| 2006/0036324 A1 | 2/2006 | Sachs et al. |
| 2006/0047283 A1 | 3/2006 | Evans, III et al. |
| 2006/0052782 A1 | 3/2006 | Morgan et al. |
| 2006/0069436 A1 | 3/2006 | Sutton et al. |
| 2006/0224088 A1 | 10/2006 | Roche |
| 2006/0247773 A1 | 11/2006 | Stamp |
| 2007/0005145 A1 | 1/2007 | Banks et al. |
| 2008/0221394 A1 | 9/2008 | Melkent et al. |
| 2009/0259107 A1 * | 10/2009 | Crenshaw et al. ............ 600/202 |
| 2009/0259108 A1 * | 10/2009 | Miles et al. .................. 600/202 |
| 2009/0306480 A1 | 12/2009 | Protopsaltis |

* cited by examiner

US 8,376,937 B2

TISSUE MONITORING SURGICAL RETRACTOR SYSTEM

FIELD OF THE INVENTION

The present disclosure is directed to a surgical retractor system. More particularly, the present disclosure is directed to a retractor system that monitors parameters indicative of the state of a patient's tissue adjacent a retractor of the retractor system.

BACKGROUND

Side effects of anterior cervical decompression and fusion procedures may include post-operative dysphagia. This condition, making swallowing difficult or impossible, can be relatively long lasting, with up to twelve percent of patients with dysphagia symptoms still having those symptoms a year after surgery. Surgeons and scientists are researching whether the incidence and recovery from dysphagia corresponds with the size of the surgical dissection, the trauma induced by retractors, and the length of the time the retractors are used to maintain an open surgical site.

Conventional retractors are placed at a surgical site and used to retract tissue based solely upon a surgeons preference and experience. A surgeon conventionally attempts to "feel" when the retractor applies excessive loading to the tissue. If the loading links to the incidence of dysphagia, it would be helpful to have a system for monitoring loading or other parameters indicative of the state of the tissue.

The systems and methods disclosed herein address one or more of the shortcomings of the prior art.

SUMMARY

These and other aspects, forms, objects, features, and benefits of the present invention will become apparent from the following detailed drawings and description.

The present disclosure is directed to a surgical retractor system for monitoring the characteristics of tissue adjacent a surgical site and communicating that information to a health care provider. The surgical retractor system may include a retractor, a sensor, and a processing system. The retractor may include a first blade for interfacing with tissue on a first side of a surgical site, a second blade for interfacing with tissue on a second side of the surgical site opposite the first side of the surgical site, and a body portion supporting the first blade relative to the second blade. The body portion may be adjustable in situ in a manner that changes tissue parameters by displacing the first blade relative to the second blade to displace tissue and provide access to a surgical site. The sensor is disposed on the retractor and is configured to measure a parameter indicative of at least one characteristic of the tissue adjacent the first or the second blade. The processing system is in communication with the sensor and configured and arranged to receive information from the sensor indicative of the measured parameter. The processing system includes a threshold stored therein indicative of excessive trauma to the tissue. The processing system is configured in a manner such that it compares the received information to the stored threshold and communicates information to the health care provider regarding the comparison.

In another aspect, the present disclosure is directed to a sensor system for use on surgical retractor system. The sensory system includes a detector for receiving a signal or stimulus that creates a signal based on the received signal or stimulus and an anchor portion shaped to removably attach to a portion of the surgical retractor system. In some aspects, the sensor system is one of a sleeve configured to receive a portion of the retractor therein, a C-shaped clip configured to clip onto the retractor, and a flexible patch having an adhesive layer therein.

In another aspect, the present disclosure is directed to a surgical retractor system for monitoring the characteristics of tissue adjacent a surgical site and communicating that information to a health care provider. The surgical retractor system may include a retractor and a tissue parameter detecting system. The retractor includes a first blade for interfacing with tissue on a first side of a surgical site, a second blade for interfacing with tissue on a second side of the surgical site opposite the first side of the surgical site, and a body portion comprising a first arm and a second arm and an adjustment element adjustably connecting the first and second arms. The first and second arms respectively support the first blade and the second blade. The adjustment element is adjustable in situ in a manner that changes tissue parameters by displacing the first blade relative to the second blade to displace tissue and provide access to a surgical site. The tissue parameter detecting system is structurally configured and arranged to measure a parameter indicative of at least one characteristic of the tissue adjacent the first or the second blade. The tissue parameter detecting system has a threshold stored therein indicative of excessive trauma to the tissue. The tissue parameter detecting system is structurally configured and arranged in a manner such that it compares the measured information to the stored threshold and communicates information to the health care provider regarding the comparison.

BRIEF DESCRIPTION OF THE DRAWINGS

The accompanying drawings serve to exemplify some of the embodiments of this invention.

DETAILED DESCRIPTION

Figure 1:
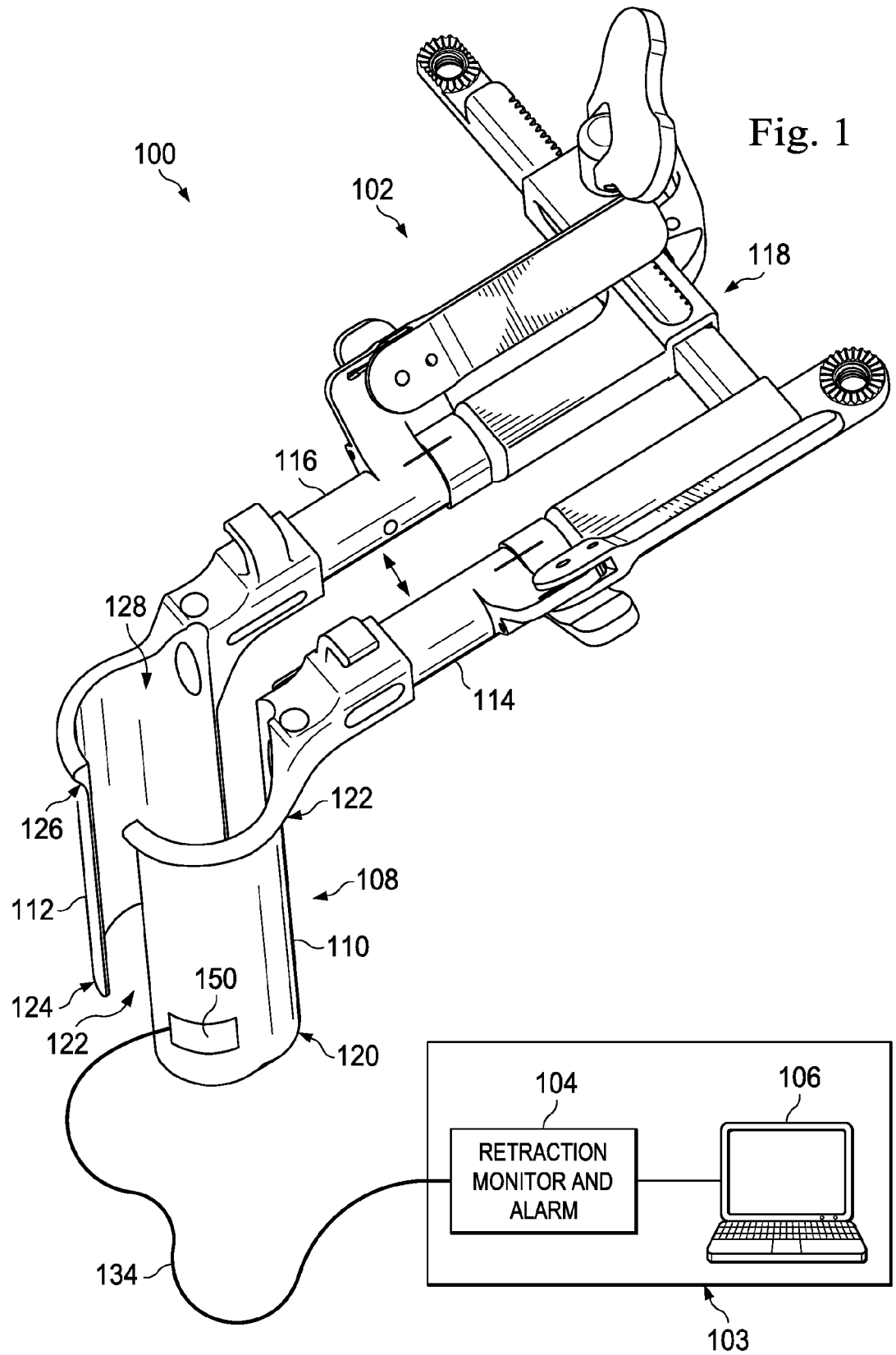
FIG. 1 is an illustration of a perspective view of a surgical retractor of the present disclosure with a sensor for detecting data indicative of the state of tissue adjacent the retractor.

The present disclosure relates generally to the field of orthopedic surgery, and more particularly to devices, systems and methods for monitoring tissue displaced by a retractor system. For the purposes of promoting an understanding of the principles of the invention, reference will now be made to embodiments or examples illustrated in the drawings, and specific language will be used to describe these examples. It will nevertheless be understood that no limitation of the scope of the invention is thereby intended. Any alteration and further modifications in the described embodiments, and any further applications of the principles of the invention as described herein are contemplated as would normally occur to one skilled in the art to which the disclosure relates.

This disclosure is directed to instruments and methods for performing percutaneous surgery, including spinal surgeries that include one or more techniques such as laminotomy, laminectomy, foramenotomy, facetectomy, discectomy, interbody fusion, spinal nucleus or disc replacement, and implant insertion including plates, rods, and bone engaging fasteners, for example. A retractor system, including a retractor, permits a surgeon to perform through a working channel or passageway through skin and tissue of the patient. The retractor is adjustable in situ to increase the size of the working channel to facilitate access to the working space at the distal end of the retractor while minimizing trauma to tissue surrounding the retractor. The retractor can be used with any surgical approach to the spine, including anterior, posterior, posterior mid-line, lateral, postero-lateral, and/or antero-lateral approaches, and in other regions besides the spine.

FIG. 1 shows an exemplary a retractor system 100, including a retractor 102 and a processing system 103 that, in this embodiment, includes a monitor 104 and a console, such as a computer system 106. The retractor 102 includes a variable width main body tube 108 formed of a first blade 110 and a second blade 112. It also includes a first arm 114 and a second arm 116 extending from the main body tube 108. These are adjustably connected to each other at a proximal end by an adjustment element 118. The adjustment element 118 adjusts the distance between the first and second arms 114, 116, and likewise, adjusts the distance between the first and second blades 110, 112.

In this embodiment, the blades 110, 112 have an arcuate cross section with a concave inner surface and a convex outer surface. In other embodiments, the blades have other configurations such as flat, curved, or other geometries. The first blade 110 has a distal end 120 and an opposite proximal end 122. The second blade 112 has a distal end 124 and an opposite proximal end 126. The distal ends 120, 124 may be beveled to facilitate insertion, although non-beveled ends are also contemplated. A working channel 128 is formed between the first and second blades 110, 112. After insertion into a patient, the working channel 128 is enlarged by spreading the first and second blades 110, 112 apart using the adjustment element 118. In this embodiment, the adjustment element 118 is a rack and pinion assembly, although outer adjustment elements are contemplated. In some examples, the adjustment element 118 comprises a motor, such as an electric, hydraulic, or pneumatic motor that spreads apart the first and second blades.

The first and second blades 110, 112 are respectively coupled with the first and second arms 114, 116 which are engaged with adjustment element 118. It should be appreciated that the blades 110, 112 may be coupled with the arms 114, 116 in any suitable arrangement, including dovetail connections, fasteners, threaded coupling members, clamping members, snap rings, compression bands, straps, ball-detent mechanisms, releasably interlocking cams or tabs, welding, fusing, and/or adhering, just to name a few possibilities. In some embodiments, the blades 110, 112 are integrally formed with the arms 114, 116. Still further, the blades 110, 112 may be removably coupled with the arms 114, 116, and alternative retractor blades may be chosen from a plurality of retractor blades to replace retractor blades 110, 112 to better suit a particular application in which the retractor 102 may be used. In addition, it should be noted that alternative embodiments use more than two plates, and in further alternative embodiments, a single blade may be used.

In use, after insertion into the patient, the working channel 128 can be enlarged by separating first retractor blade 110 and second retractor blade 112. Separation of the retractor blades 110, 112 increases the size of working channel 128. However, as with any invasive surgery, this separation applies some level of stress and trauma to the tissue about the surgery site.

Figure 2:
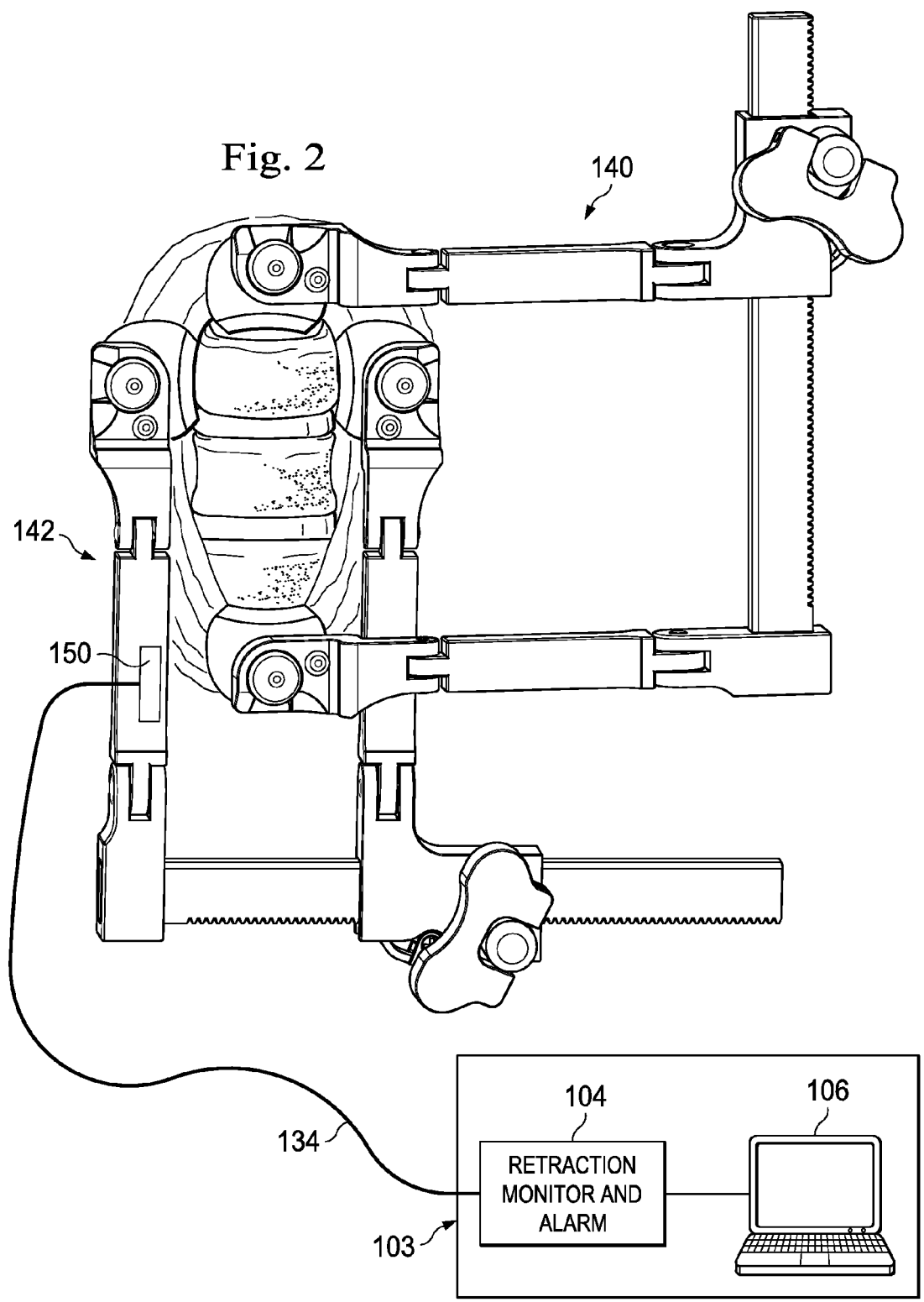
FIG. 2 is an illustration of a top view of two surgical retractors in a surgical application, one of the surgical retractors having a sensor thereon and in communication with a retraction monitor and system in accordance with the disclosure of FIG. 1.

FIG. 2 is a top view showing two retractors 140, 142, respectively, in use at a surgical site to maintain or retract tissue in a position providing surgical access according to an exemplary aspect of the present disclosure. Here, the retractors 140, 142 are similar in many respects to the retractor 102 described above, and for efficiency, will not be re-described in great detail. It is sufficient to note that the retractors 140, 142 each include first and second blades, arms, and an adjustment element that controls the separation between the arms and blades.

To quantify the level of stress and trauma to the tissue at the surgical site, each of the retractor 102 in FIG. 1 and the retractor 140 in FIG. 2 includes a sensor 150 associated therewith. The sensor 150 provides information indicative of one or more parameters of the loading stress, trauma, status, or other parameter of the tissue at the surgical site. For example, the sensor 150 may provide information including mechanical, thermal, chemical fluidity (such as pressure, time, heat, blood flow, lactid acid build-up, or other parameters) determined to be useful in a surgical setting. In the embodiment in FIG. 1, the sensor 150 is disposed upon the blade 110 of the retractor 102. Accordingly, in addition to sensing the pressure on the blade 110, the sensor may interface directly with the tissue and may provide information relating to either the state of the retractor or directly measure parameters of the tissue. In some examples, a sensor 150 may be used on each blade. In other examples, the sensor 150 may be used only on a single blade. The blade may be the medial blade, responsible for retracting the midline structures from the anterior aspect of the spine. For example only, the sensor 150 may be a strain sensor, a thermocouple, a flow meter such as a Transonic VLF-21 Laser Doppler Flowmeter, other sensors, or a plurality of sensors arranged in a manner known in the art.

In the embodiment in FIG. 2, the sensor 150 is disposed upon a retractor arm of the retractor 142. In this embodiment, the sensor 150 is a strain sensor arranged to sense the arm strain indicative of pressure applied to the retractor blade 110 by patient tissue during use.

In either case, the monitor 104 is structurally configured to receive information from the sensor 150. In the embodiment shown, the monitor 104 is connected to the sensor 150 via a wired connection 134. Signals transmitted over the wired connection 134 provide information that may be filtered or processed to identify information gathered by the sensor 150.

Figure 3:
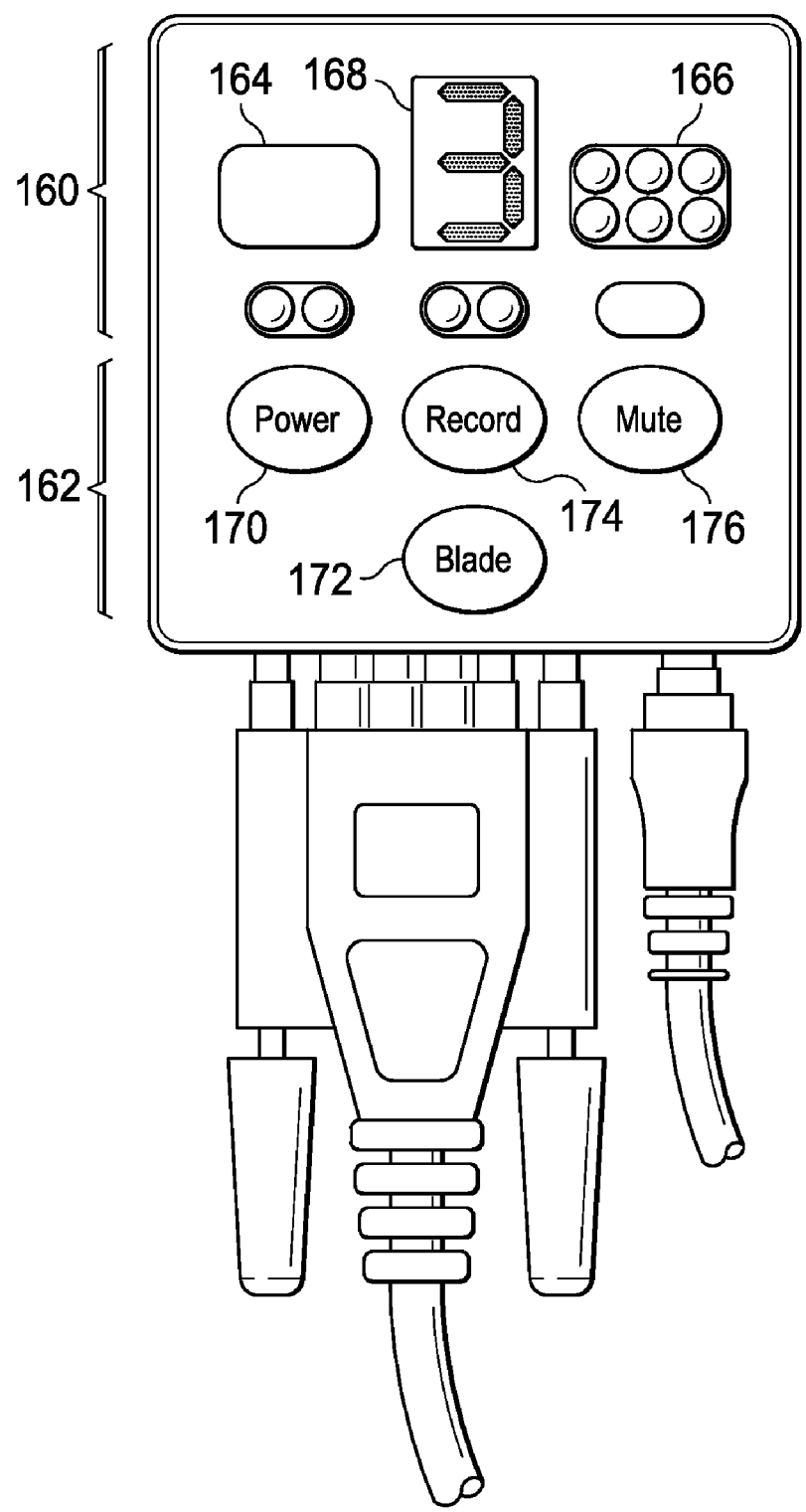
FIG. 3 is an illustration of an exemplary retraction monitor connectable to the sensor in FIGS. 1 and 2.

FIG. 3 shows an exemplary monitor 104. It includes both a display portion 160 and an input portion 162. The display portion includes a visual indicator 164 labeled "Normal," a visual indicator 166 labeled "Alarm," and a visual indicator 168 labeled "Blade Size." The display portion 160 provides real time feedback based on information received from the sensor indicative of the level of tissue trauma. For example, the monitor 104 may indicate that the received information indicates that the tissue at the surgical site is subject to trauma above or below a pre-established threshold. In some embodiments, the monitor 104 is configured to be operable with different blade sizes, and the threshold value may be different based on the retractor blade size.

When the Normal visual indicator 164 is active, the sensor information is indicative of trauma levels below a preset threshold. In some instances the threshold value level is configured to automatically adjust over time. For example, the monitor 104 may be programmed so that the threshold decreases over a surgical period, such that even a lower level of trauma is not maintained too long.

When the Alarm visual indicator 166 is active, the sensor information is indicative of trauma levels above a preset threshold. This alerts the surgeon to reduce the pressure on the tissue at least for a period of time. In addition to a visual Alarm indicator, the monitor includes an audible indictor. Further, some embodiments include a tactile indicator where the monitor 104 vibrates as an alarm indicator. Also, in some embodiments, the visual indicators have color-based lighting schemes, for example, with green indicating that measured parameters are below a threshold, red indicating that measured parameters are above a threshold, and flashing red or yellow indicating that tissue should be relaxed for a period of time. Other alarm schemes are also contemplated. Accordingly, the surgeon may be alerted to over-trauma levels in any of multiple ways.

The input portion 162 of the monitor 104 includes a power selector 170, a blade selector 172, a record selector 174, and a mute selector 176. These are shown as buttons, but may be icons on a touch screen, or may be selectable by a mouse, keyboard, or other input device. The record selector 174 turns on a recorder that records the feedback from the sensor 150. The recorder may be a microcomputer or chip capable of receiving, recording, or processing information communicated by the sensor 150 on the retractor 102.

In some examples, the monitor 104 is configured to monitor retraction force/pressure and force/pressure vs. time. In other examples the monitor is configured to monitor temperature, chemical fluidity (e.g., pressure, time, heat, blood flow, lactid acid build-up) or other parameters.

In some embodiments, the monitor 104 is also a safety mechanism. For example, when a detected sensor signal exceeds a pre-established threshold, then in addition to the alarm system being activated as described above, a safety mechanism may be activated. This may include automatically controlling the retractor to relieve pressure on the tissue. This may cooperate with retractors having an automatic distraction control as is disclosed in U.S. Patent Publication No. 2009/0306480, filed Jun. 6, 2008, incorporated herein by reference. The automatic control may provide a gradual reduction in pressure by distracting the blades, may provide oscillation, or massaging vibration, or other safety mechanisms that provide relief to the tissue. As the pressure decreases, the alarm function on the monitor 104 may likewise adjust, such as changing from a solid light indicator to a flashing indicator, for example.

In the embodiment shown, the monitor 104 connects to the computer system 106. This may be a personal computer or other computer system, and may include its own input devices, such as a keyboard, mouse, and other standard input devices. The computer system 106 may further process the sensor signal and may provide graphs or additional information indicative of the information detected by the sensor. In some embodiments, the computer system 106 is component that records the detected information when the record input is selected on the monitor 104. In some embodiments the monitor 104 and computer system 106 are combined into a single unit that monitors the tissue. In other embodiments, the computer and the monitor are used independently of each other, without being attached together.

FIGS. 4-7 disclose sensor systems for removably attaching the sensor 150 to the retractor 102. Accordingly, in some embodiments, the sensor system may be removed and discarded after use and before the retractor is sterilized.

Figure 4:
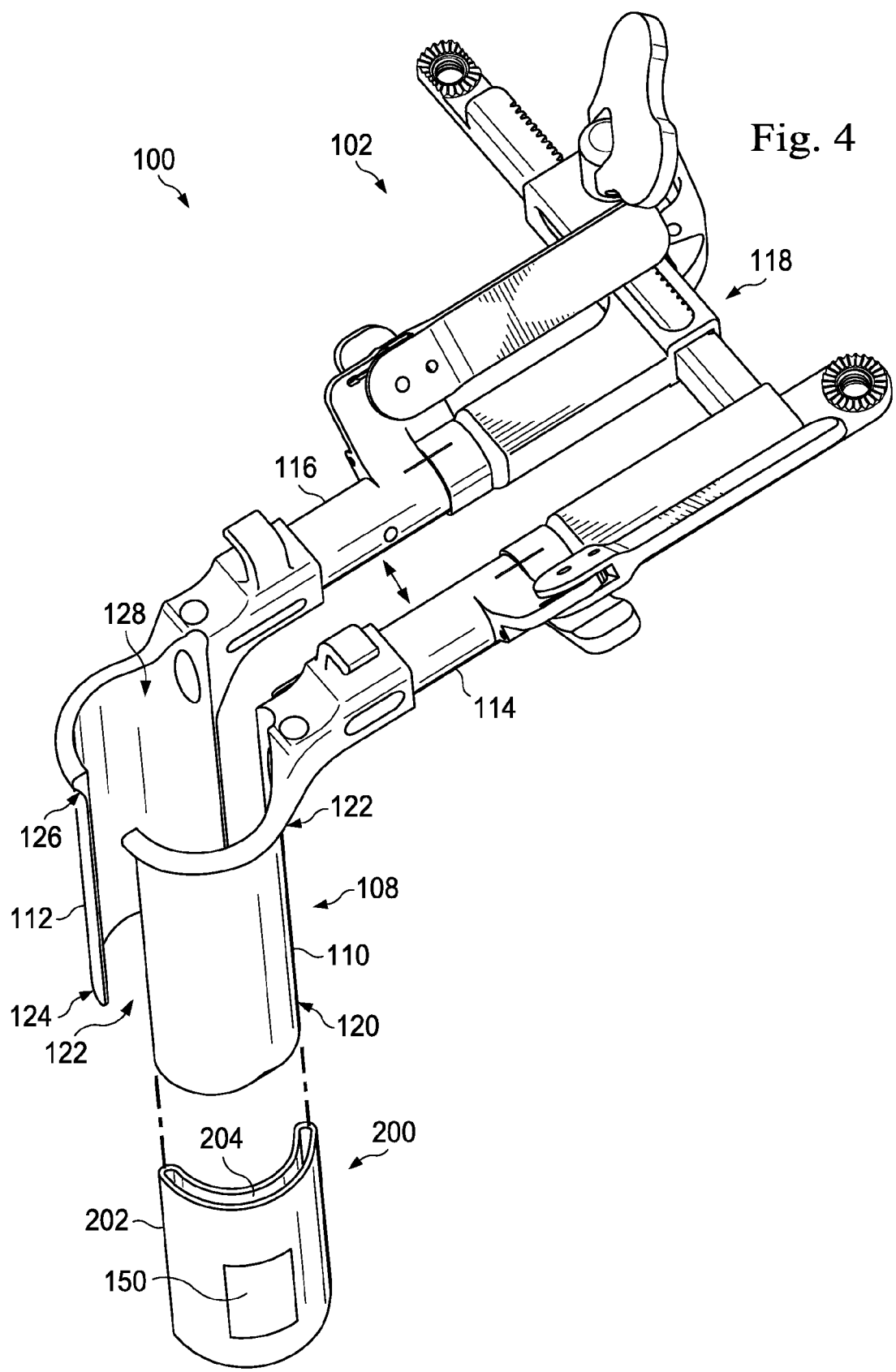
FIG. 4 is an illustration of a sensor system in the form of a sensor sleeve having a built-in sensor in accordance with the present disclosure.

FIG. 4 discloses a sensor system 200 including an anchor portion for attachment to the retractor 102 and the sensor 150. In this embodiment, the anchor portion is a sleeve 202. The sleeve 202 includes at least one end with an opening 204 for receiving at least part of the retractor 102. Accordingly, the sleeve 202 may be sock-like, with a single open end, or may be tube-like, with two open ends. In this embodiment, the sleeve 202 is sized and shaped to receive at least a part of the first blade 110. In some embodiments, it is formed to have a particular shape matching the retractor 202, while in other embodiments, the sleeve 202 is configured of a conformable material, such as a fabric, that may conform to the shape of the retractor 102. The disposable sleeve 202 can be made of any suitable material, including flexible or elastic polymers, such as polyurethane, silicone, and rubber, among many others.

In some embodiments, the sensor 150 is built into or embedded within the sleeve 202 such that the sensor 150 is applied against the retractor 102, and configured to measure a particular parameter of the retractor 102. For example, the sensor 150 may be configured to measure, for example only, force, displacement, contact stress, torque deflection, tension, compression, strain, and pressure on the retractor 102. In other embodiments, the sensor is associated with the sleeve in a manner that enables it to measure parameters of the tissue adjacent the sleeve. For example, the sensor 150 may be configured to measure temperature, pressure, blood flow, lactid acid build-up, or other parameters. When placed on the retractor, the sleeve 202 and the sensor 150 are configured to cooperate with the processing system 103 to record and/or process the pressure or strain information communicated from the sensor 150 during the surgery.

It is worth noting that the more than one disposable sleeve may be used with the retractor 102 at a single time. For example, the blades 110, 112 may each by outfitted with a sleeve-type sensor system 200. Further, each sleeve 202 may include more than one sensor 150 disposed thereon for measuring more than one parameter. These may be sensors of the same or different types. As explained above, the sensors 150 may include one or more of any those that measure the following data: temperature, force, displacement, contact stress, torque deflection, tension, compression, pressure, and strain, among others. The disposable sensors 150 may track, record, transmit, or store the above data as a function of time.

Figure 5:
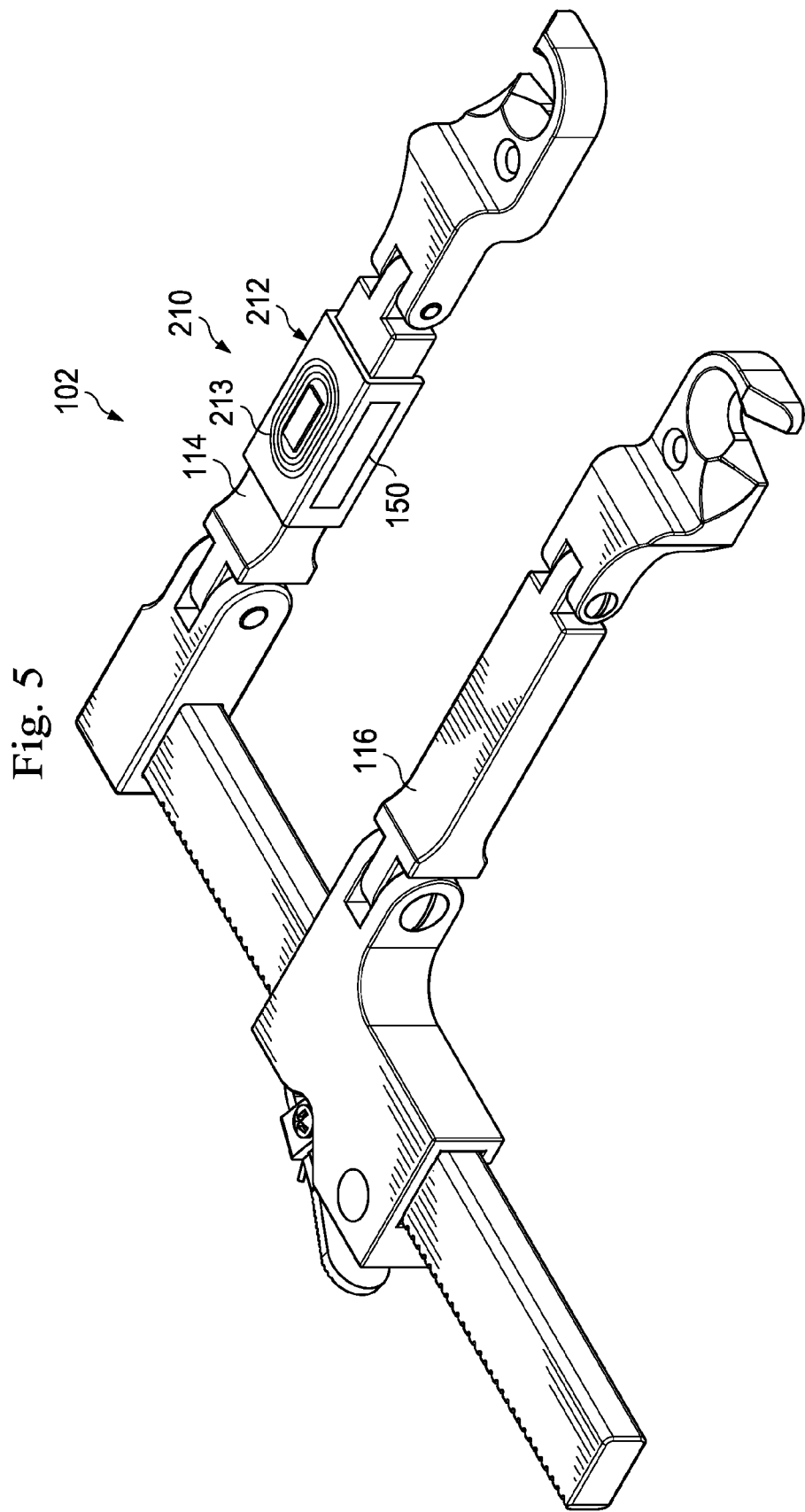
FIG. 5 is an illustration of a sensor system in the form of a clip having a built-in sensor in accordance with the present disclosure.
Figure 6:
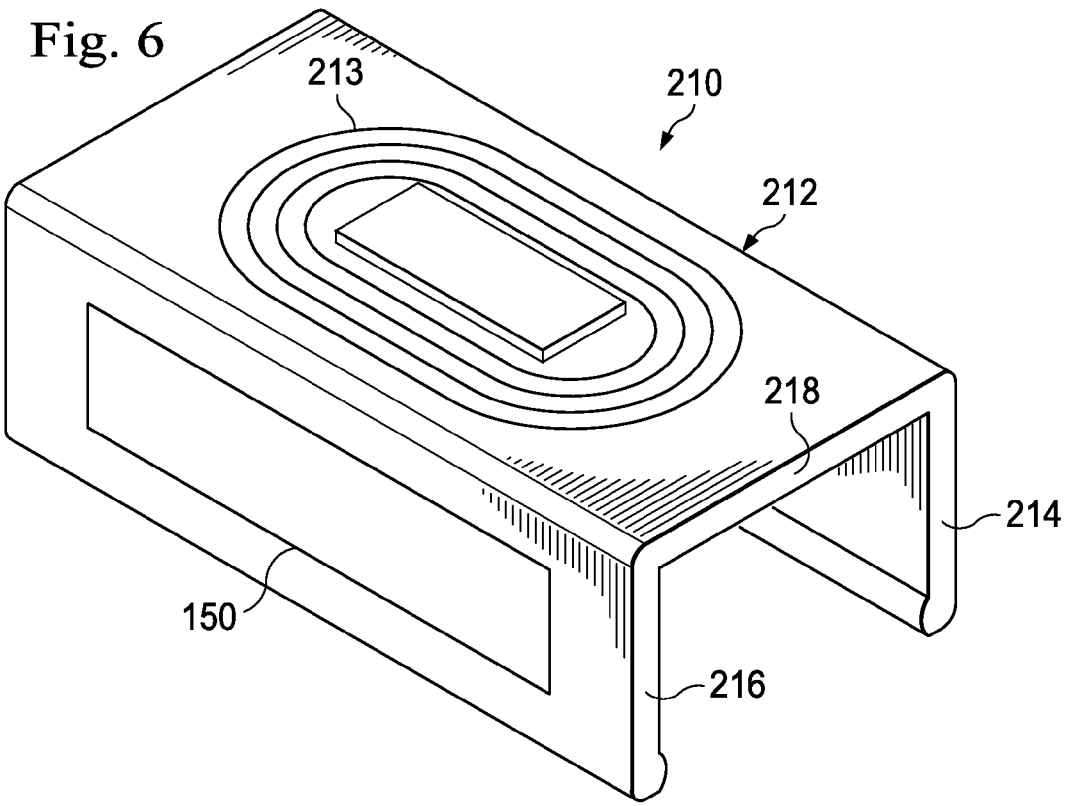
FIG. 6 is an illustration of the sensor system in FIG. 5.

FIG. 5 shows another embodiment of a retractor 102 with a first arm 114, a second arm 116, and a sensor system 210 for removable attachment to the retractor. In this embodiment, the sensor system 210 includes an anchor portion as a flexible C-shaped clip that snaps onto the retractor. In FIG. 5, the sensor system 210 is attached to the first arm 114, but may be configured to attach to any suitable portion on the retractor 102. FIG. 6 shows the sensor system 210 in greater detail. As can be seen, the sensor system 210 comprises the clip body 212, a sensor 150, and in this embodiment, a coil 213 for wireless transmission using inductive coupling, explained further below. Here, the clip body 212 includes two legs 214, 216 and a side 218 that together form a C-shape. A lip 220 at the ends of the legs 214, 216 permits the clip body 212 to snap onto the retractor 102, securing it in place. The clip body 212 can be made of any suitable material, including flexible or elastic polymers, such as polyurethane, silicone, and rubber, among many others.

In some embodiments, the sensor 150 is built into or embedded within the body 212 such that the sensor 150 is applied against the retractor 102 and configured to measure a particular parameter of the retractor 102, as explained above. In other embodiments, the sensor 150 is associated with the clip body 212 and the retractor 102 in a manner that enables it to measure parameters of the tissue adjacent the clip body, as explained above. When placed on the retractor, the sleeve 202 and the sensor 150 are configured to cooperate with the processing system 103 to record and/or process the pressure or strain information communicated from the sensor 150 during the surgery.

Figure 7:
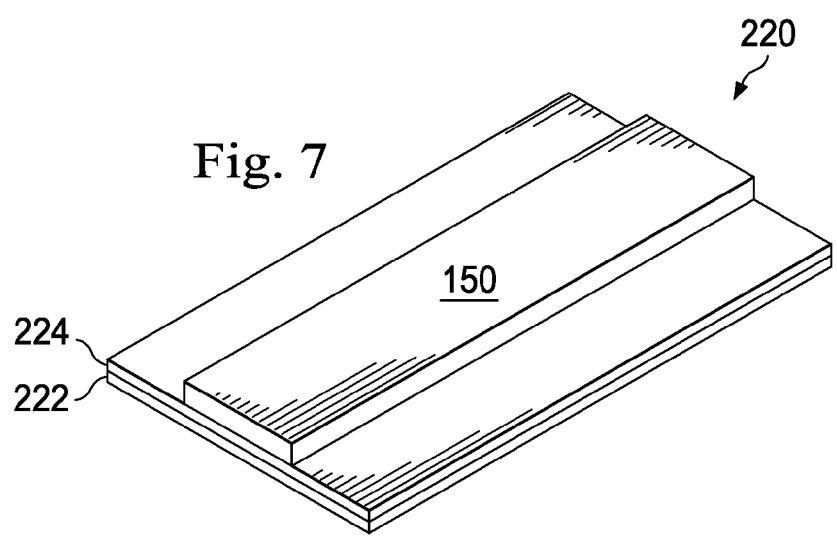
FIG. 7 is an illustration of a sensor system in the form of an adhesive patch having a built-in sensor in accordance with the present disclosure.

FIG. 7 shows another sensor system 220 as an adhesive patch. This sensor system 220 includes an anchor portion for removable attachment to the retractor 102 in the form of an adhesive layer 222. The adhesive patch includes the adhesive layer 222, a backing layer 224, and the sensor 150. The adhesive layer 222 may be formed of any adhesive that securely holds the sensor 150 in place and that can be removed from the retractor 102 prior to sterilization. The backing layer 224 may be a flexible woven or non-woven material. The sensor system 220 may be placed either on the blade to be contact with tissue or on the retractor arm, out of contact with the tissue. This sensor system 220 may be removed from a sterile packet and attached to an appropriate location on the retractor.

In all the embodiments in this disclosure, more than one sensor may be used at the same time in the same region or different regions of the retractor, for measuring the same parameter or for measuring different parameters. Accordingly, the sensor systems as well as directly placed sensors as in FIG. 1, may include a plurality of sensors 150. As explained above, the sensors 150 may include one or more of any sensors that measure the following data: temperature, force, displacement, contact stress, torque deflection, tension, compression, pressure, and strain, among others. The disposable sensors 150 may track, record, transmit, or store the above data as a function of time.

Figure 8:
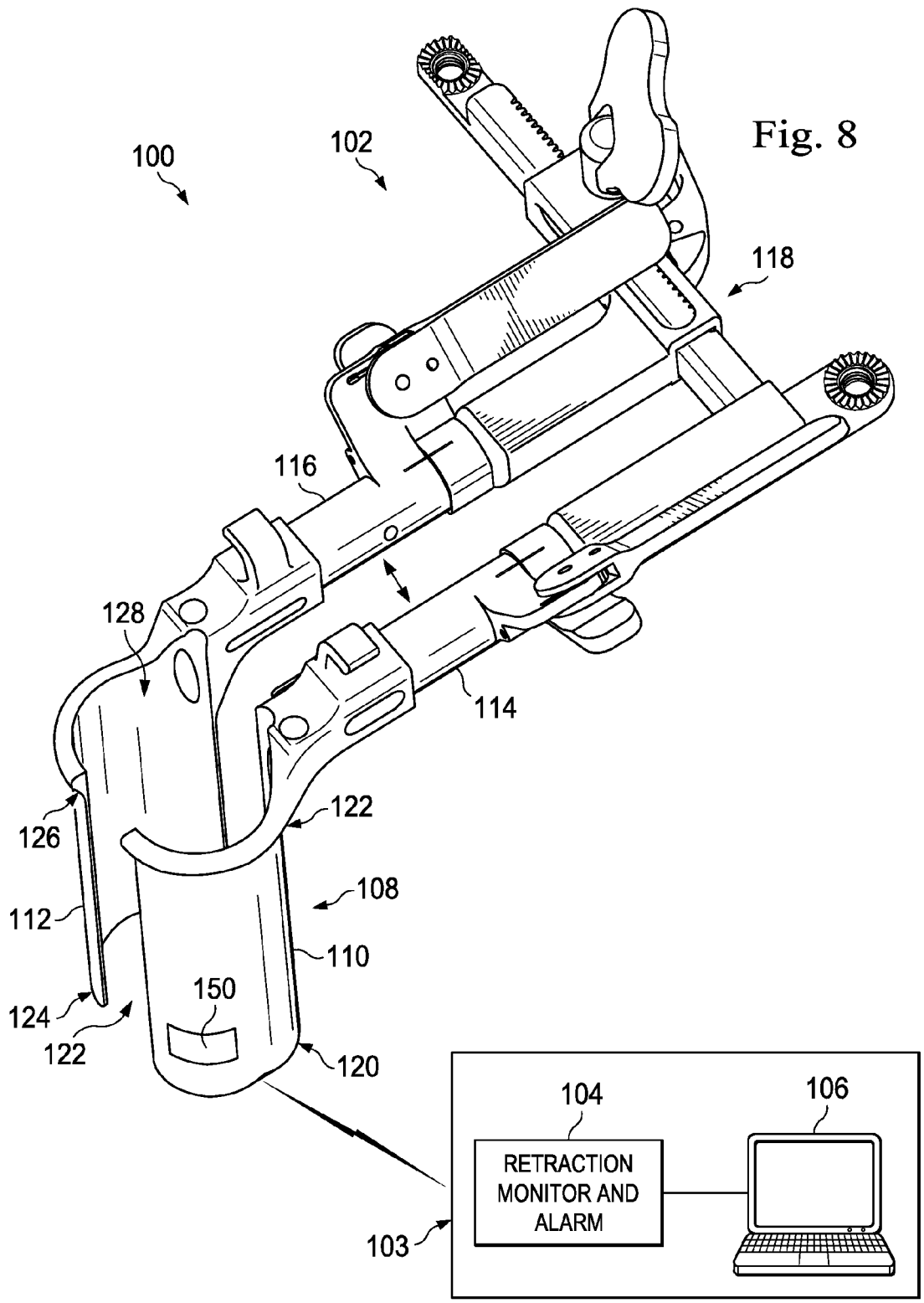
FIG. 8 is an illustration of a perspective view of a surgical retractor of the present disclosure with a sensor for detecting data indicative of the state of tissue adjacent the retractor usable in a wireless environment.

FIG. 8 shows another embodiment of the of the retractor in FIG. 2. In this embodiment, instead of employing a wired communication system, the device employs a wireless communication between the sensor 130 and the monitor 104. Accordingly, the information collected by the sensor 130 may be communicated via a wireless transmission the monitor 104. This wireless communication may be accomplished via any suitable wireless method, including RF, Bluetooth, inductive, coupling, transmissions via ultrasound, microwave, or other ranges and frequencies.

Figure 9:
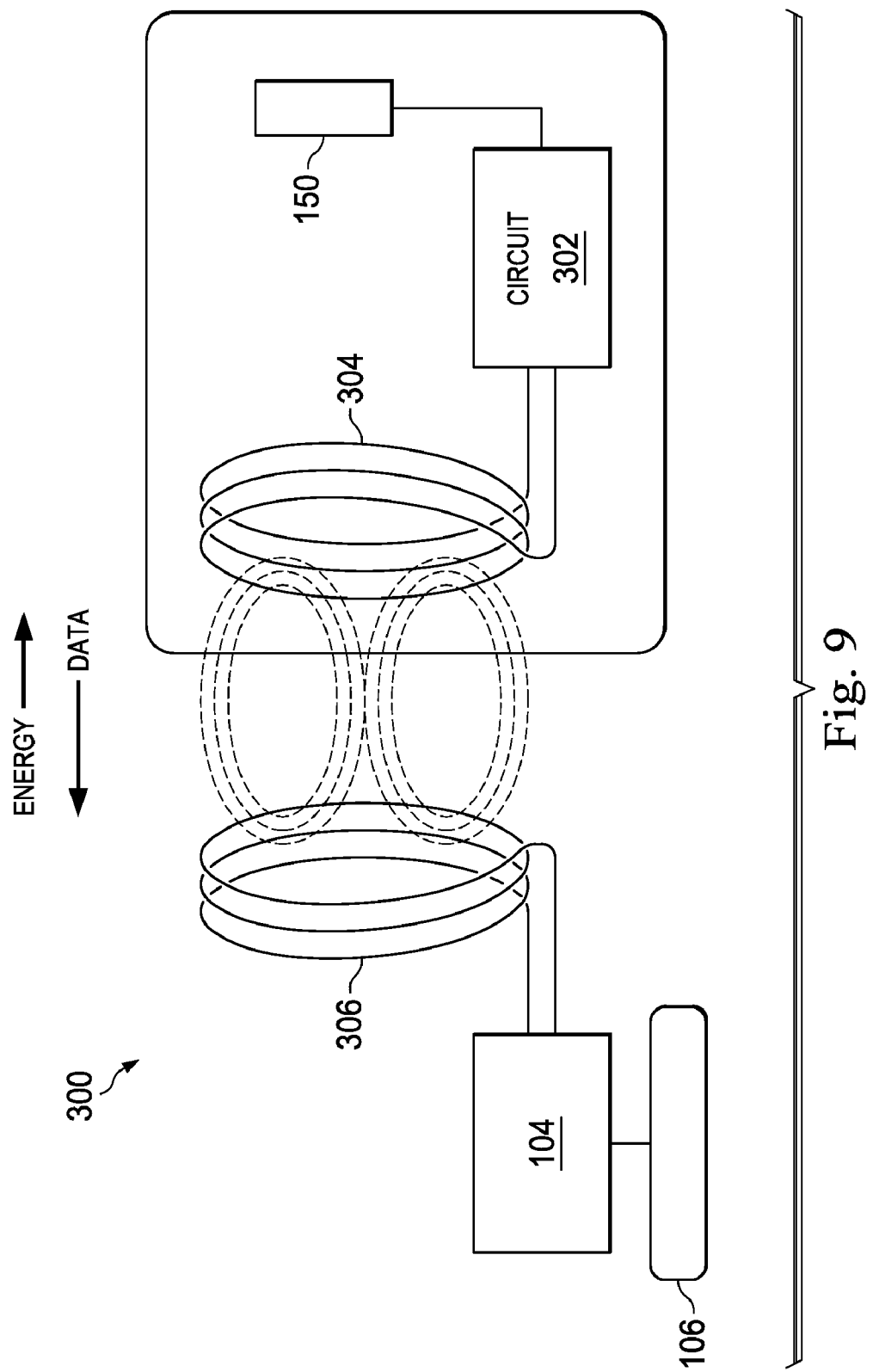
FIG. 9 is a diagram of an exemplary wireless transmission system using inductive coupling.

FIG. 9 discloses one example of a wireless system 300 for communicating between the sensor 150 and the monitor 104. This embodiment uses inductive coupling to wirelessly power the sensor and retrieve data. Here, the sensor or sensor system comprises the sensor 150, circuitry 302, and a transmission coil 304. The monitor 104 comprises a reader coil 306 as an inductive antenna. The reader coil 306 need not be contained within the monitor housing, but may extend from the housing for placement somewhere adjacent the surgical site. The reader coil 306 and the transmission coil 304 cooperate by transfer data and energy. In use, the reader coil 306 supplies energy to the transmission coil 304. This in turn powers the circuit 302 and retrieves data from the sensor 150. This information maybe processed at the sensor or may be wirelessly transmitted from the transmission coil 304. Once received, the information may be processed as described above.

Wireless communications other than those described above also may be used. For example, the sensor 150 may be associated with a power source and transmitter disposed on the retractor 102. Accordingly, the range of the wireless transmitted signals may be greater than when inductive coupling is used. In some instances, the sensor 150 may be a passive sensor, while in other embodiments, the sensor 150 may be an active sensor. In addition, the sensor may be either a one way or two way sensor, and may be internally powered or externally powered. In some aspects, the sensors are connected to an antenna for improved wireless signaling. As described above, the sensor 150 may be either disposable or non-disposable. All the features described above are also relevant when wireless technology is used to transmit and process information. For example, even using wireless technology, the monitor 104 or computer system 106 may, record and interpret data.

In use, a surgeon makes an incision into a patient. If a sensor is not attached to the retractor, the surgeon may attach the sensor. As described above, this may be accomplished by attaching a removable and flexible sleeve including the sensor about a portion of the retractor, attaching a clip including the sensor, or adhering an adhesive patch including the sensor. Other attachment methods are contemplated.

With the retractor prepared, the surgeon inserts the retractor blades into the incision. In some examples, the blades are formed to create a working channel between them. In other examples, the adjustment element spreads apart the arms and blades, and the spreading blades spread the tissue, creating a working channel. During this spreading step and/or with the blades in place against the tissue, the sensor detects changes in measurable parameters indicative of the state of the tissue adjacent the blades. As described above, the measurable parameter may be strain on the blades or arm, direct force on the blades, pressure, temperature, or any of the other listed or unlisted parameters.

The monitor receives signals from the sensor with information indicative of the measured parameter. In some embodiments, the monitor stores a threshold value for the retractor that coincides with a value beyond which there is an increased risk of tissue damage. The monitor may compare the received information with the stored threshold. If the received information exceeds the threshold, the monitor may give a warning as discussed above. For example, the warning may be activated with a pressure greater than 100 mmHg has been sustained for more than 15 minutes or when a pressure greater than 50 mmHg has been sustained for more than 30 minutes.

The monitor or an associated computer system also may record the information and display graphs or charts indicative of the measured parameters of the status of the tissue.

While the present invention has been illustrated by the above description of embodiments, and while the embodiments have been described in some detail, it is not the intention of the applicant to restrict or in any way limit the scope of the invention to such detail. Additional advantages and modifications will readily appear to those skilled in the art. Therefore, the invention in its broader aspects is not limited to the specific details, representative apparatus and methods, and illustrative examples shown and described. Accordingly, departures may be made from such details without departing from the spirit or scope of the applicant's general or inventive concept. It is understood that all spatial references, such as "longitudinal axis," "horizontal," "vertical," "top," "upper,"

"lower," "bottom," "left," and "right," are for illustrative purposes only and can be varied within the scope of the disclosure.

What is claimed is:

1. A surgical retractor system for monitoring the characteristics of tissue adjacent a surgical site and communicating that information to a health care provider, comprising:
    a retractor comprising
        a first blade for interfacing with tissue on a first side of a surgical site;
        a second blade for interfacing with tissue on a second side of the surgical site opposite the first side of the surgical site;
        a body portion supporting the first blade relative to the second blade, the body portion being adjustable in situ in a manner that changes tissue parameters by displacing the first blade relative to the second blade to displace tissue and provide access to a surgical site;
    a sensor disposed on the retractor, the sensor being configured to measure a parameter indicative of at least one characteristic of the tissue adjacent the first or the second blade;
    a sensor system comprising a removable sleeve sized and shaped to extend about one of the first and second blades of the retractor, the removable sleeve comprising the sensor configured to measure the parameter indicative of at least one characteristic of the tissue; and
    a processing system in communication with the sensor configured and arranged to receive information from the sensor indicative of the measured parameter, the processing system having a threshold stored therein indicative of excessive trauma to the tissue, the processing system being configured in a manner such that it compares the received information to the stored threshold and communicates information to the health care provider regarding the comparison.

2. The surgical retractor system of claim 1, wherein the processing system comprises one of a visual alert and an audible alert, and wherein the processing system activates the one of the visual and audible alerts when the received information exceeds the threshold.

3. The surgical retractor system of claim 1, wherein the processing system comprises a recording system that is configured and arranged to record the information received from the sensor.

4. The surgical retractor system of claim 1, wherein the processing system comprises a monitor and computer system.

5. The surgical retractor system of claim 1, wherein the processing system comprises a monitor remote from the computer system that functions to initiate recording on the computer system.

6. The surgical retractor system of claim 1, wherein the retractor body portion comprises a first arm and a second arm extending respectively from the first and second blades, the sensor being configured to measure strain on the first arm indicative of the force on the tissue adjacent the blades.

7. The surgical retractor system of claim 1, wherein the sensor is removable from the retractor.

8. The surgical retractor system of claim 7, wherein the sensor is a part of the removable sleeve.

9. The surgical retractor system of claim 1, wherein the processing system comprises a computer.

10. The surgical retractor system of claim 1, comprising a wireless communication system configured to wirelessly transmit the information from the sensor to the processing system.

11. The surgical retractor system of claim 1, wherein the removable sleeve is formed of a flexible material configured to conform to the shape of said one of the first and second blades of the retractor.

12. A surgical retractor system for monitoring the characteristics of tissue adjacent a surgical site and communicating that information to a health care provider, comprising:
    a retractor comprising
        a first blade for interfacing with tissue on a first side of a surgical site;
        a second blade for interfacing with tissue on a second side of the surgical site opposite the first side of the surgical site;
        a body portion comprising a first arm and a second arm and an adjustment element adjustably connecting the first and second arms, the first and second arms respectively supporting the first blade and the second blade, the adjustment element being adjustable in situ in a manner that changes tissue parameters by displacing the first blade relative to the second blade to displace tissue and provide access to a surgical site;
    a tissue parameter detecting system comprising a sensor structurally configured and arranged to measure a parameter indicative of at least one characteristic of the tissue adjacent the first or the second blade, the tissue parameter detecting system having a threshold stored therein indicative of excessive trauma to the tissue, the tissue parameter detecting system being structurally configured and arranged in a manner such that it compares the measured information to the stored threshold and communicates information to the health care provider regarding the comparison; and
    a sensor system comprising a removable sleeve sized and shaped to extend about one of the first and second blades of the retractor, the removable sleeve comprising the sensor configured to measure the parameter indicative of at least one characteristic of the tissue.

13. The surgical retractor system of claim 12, wherein the tissue parameter detecting system comprises:
    a strain sensor disposed on one of the first arm and the first blade of the retractor, the strain sensor being configured to measure strain applied to the one of the first arm and the first blade by the tissue adjacent the first blade; and
    a processing system in communication with the sensor and configured and arranged to receive the information from the sensor indicative of the strain, the processing system having the threshold stored therein indicative of excessive trauma to the tissue, the processing system being configured in a manner such that it compares the received information to the stored threshold and communicates information to the health care provider regarding the comparison.

14. The surgical retractor system of claim 12, wherein the first and second blades each have an arcuate cross section with a concave inner surface and a convex outer surface configured to engage tissue, the inner surface of the first blade facing the inner surface of the second blade so as to define a substantially circular working channel.

15. The surgical retractor system of claim 12, wherein the sensor configured to measure the parameter indicative of at least one characteristic of the tissue comprises more than one sensor for measuring more than one parameter.

16. The surgical retractor system of claim 12, wherein the sensor is embedded within the sleeve such that the sensor is applied against the retractor.

* * * * *